(12) United States Patent
Engel

(10) Patent No.: US 6,752,801 B2
(45) Date of Patent: Jun. 22, 2004

(54) METAL PROBE FOR INTRACORPOREAL CALCULI CRUSHING

(75) Inventor: Konrad Engel, Sonnbichl 12- D-83674, Gaissach (DE)

(73) Assignee: Konrad Engel, Gaissach (DE)

( * ) Notice: Subject to any disclaimer, the term of this patent is extended or adjusted under 35 U.S.C. 154(b) by 0 days.

(21) Appl. No.: 10/185,463

(22) Filed: Jun. 27, 2002

(65) Prior Publication Data

US 2002/0165558 A1 Nov. 7, 2002

Related U.S. Application Data

(63) Continuation of application No. 09/402,970, filed as application No. PCT/EP98/02077 on Apr. 9, 1998.

(30) Foreign Application Priority Data

Apr. 15, 1997 (DE) .......................................... 197 15 698

(51) Int. Cl.[7] .............................................. A61B 17/22
(52) U.S. Cl. ............................ 606/2.5; 606/128; 601/4; 604/22; 600/101; 600/104
(58) Field of Search .............................. 606/2.5, 41, 46, 606/128, 197; 241/1; 250/492.1; 600/101, 191, 200, 224, 104, 105; 601/2, 4; 604/19, 20, 22

(56) References Cited

U.S. PATENT DOCUMENTS

| 3,823,717 A | * | 7/1974 | Pohlman et al. ............. 128/305 |
|---|---|---|---|
| 4,046,150 A | * | 9/1977 | Schwartz et al. ........... 128/328 |
| 4,589,415 A | | 5/1986 | Haaga |
| 4,721,107 A | | 1/1988 | Bolg et al. |
| 4,774,947 A | | 10/1988 | Falk et al. |
| 5,135,534 A | | 8/1992 | Tulip |
| 5,176,677 A | | 1/1993 | Wuchinich |
| 5,281,231 A | | 1/1994 | Rosen et al. |
| 5,951,570 A | | 9/1999 | Leibersperger et al. |
| 6,440,123 B1 | * | 8/2002 | Engel .......................... 606/2.5 |

FOREIGN PATENT DOCUMENTS

| DE | 2 032 501 | | 1/1972 | |
| DE | 002032501 A | * | 1/1972 | |
| DE | ED 002256127 | | 11/1972 | |
| DE | 7 705 947 | | 6/1977 | |
| DE | 3 707 567 | | 9/1987 | |
| EP | 0 331 313 | | 2/1989 | |
| FR | 002317903 A | | 2/1977 | |
| WO | WO 93/16646 | * | 9/1993 | ........... A61B/17/20 |

* cited by examiner

Primary Examiner—Linda C. M. Dvorak
Assistant Examiner—A. Farah
(74) Attorney, Agent, or Firm—RatnerPrestia

(57) ABSTRACT

A metal probe for intracorporeal calculi crushing has a point at its distal end with one or several lateral notches next to the probe end. These notches secure a calculus laterally against an adjacent duct wall and thus prevent it from drawing aside when it is crushed by the notch.

9 Claims, 2 Drawing Sheets

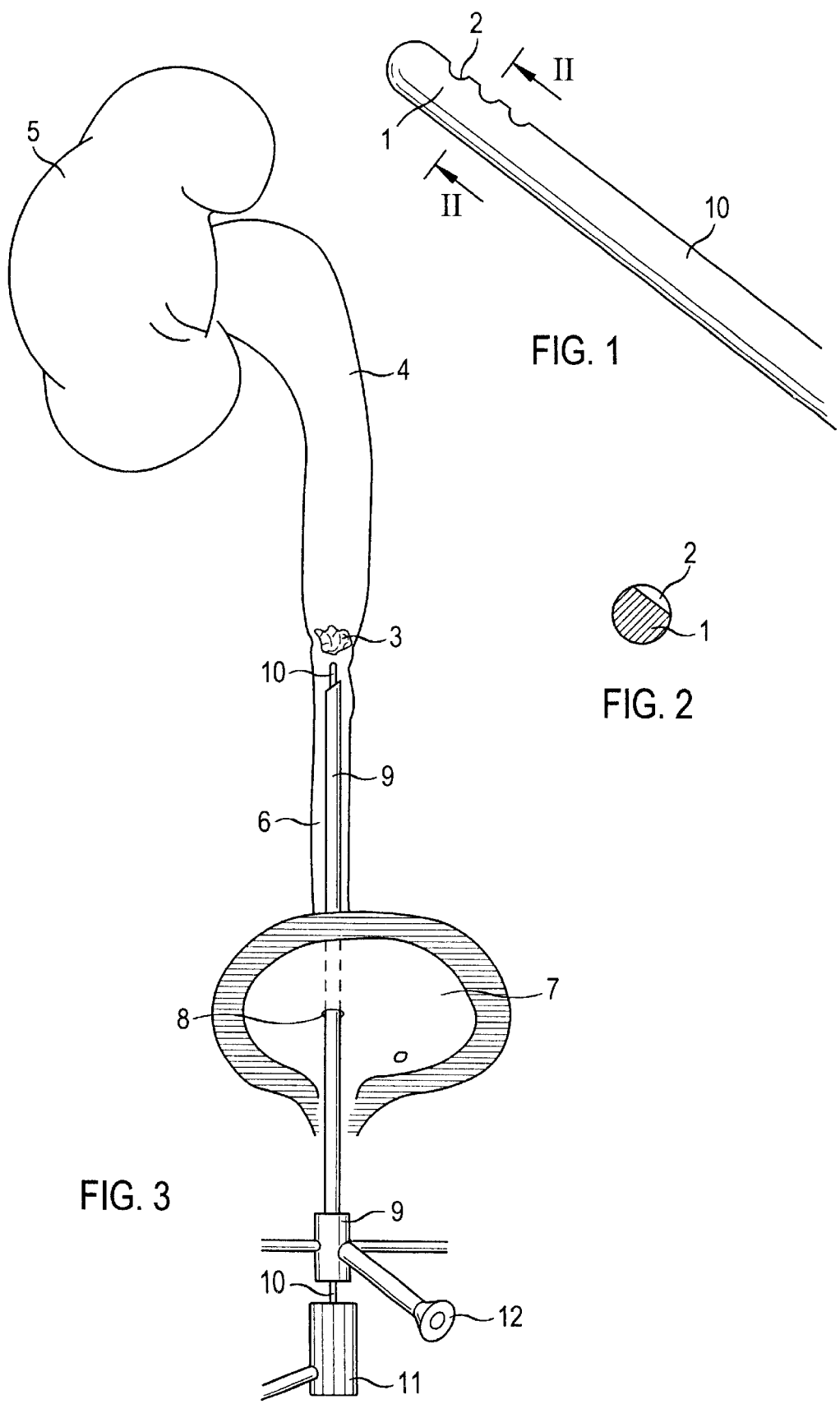

METAL PROBE FOR INTRACORPOREAL CALCULI CRUSHING

This application is a continuation of U.S. application Ser. No. 09/402,970 filed Oct. 12, 1999, now U.S. Pat. No. 6,440,123 B1, which is the U.S. national-phase application of PCT International Application No. PCT/EP98/02077 filed Apr. 9, 1998.

The present invention relates to a metal probe adapted to be introduced into the lumen of an endoscope for use in intracorporeal lithotripsy, whereon a probe tip constituting a distal end of the probe being used for crushing calculi by shock waves which are transferred by means of the probe and which result from an impact energy transferred to the proximal end of the probe for transmission.

Metal probes of the aforementioned kind are used, for instance, in a lithotripter presenting a configuration in accordance with the European Patent EP 0 317 507 B1. In these lithotripters the impact energy transferred to the probe for transmission is obtained from the impact pulse produced by a pneumatically driven impact element on a probe head having an enlarged cross-section on the proximal end of the probe so that the resulting shock wave passing through the probe is used to achieve a uniform straight motion of the probe tip. This shock wave may be used for a process of intracorporeal crushing calculi such as nephroliths, uric acid calculi or cystoliths, which is performed by means of the employed endoscope.

The probes so far used, for instance, for crushing urethroliths comprise a comparatively blunt tip by which they hit on the calculus initially fixed by the uretral wall in a largely orthogonal direction. In this step it happens frequently that the calculus becomes detached from its fixation during the action of the shock waves and is tossed in a direction towards the kidney because in most cases the ureter is distinctly enlarged above the calculus under the action of the urine flowing in from the kidney. Therefore often the attempt is made to avoid such a calculus propulsion, which is undesirable for calculus crushing, by a supplementary fixation of the calculus, specifically by so-called "basketing" wherein a basket-like calculus catcher, a so-called "Dormia basket", is additionally advanced into the ureter.

This calculus propulsion, which is hence inexpedient for the work with such probes and which can at most be counteracted with such expensive auxiliary provisions, is subject to another impairment to the extent of the ureteroscopes available for crushing urethroliths. In these ureteroscopes roughly half of the cross-section, which has a maximum width up to 4 mm (12 Charriere) on the distal end, is required for an operating duct receiving the probe whilst the other half of the cross-section receives a rigid rod-shaped optical system or also semi-rigid fibre glass filaments and bunches of individual optical fibres. This optical system, which is disposed laterally and hence not in the centre of the cross-section, dos not present a substantial wide-angle effect so that the tip of the probe advanced into the ureteroscope becomes visible only on the edge of the visual field along the uretral wall. Therefore mostly a slight tilt of the ureteroscope is required for placement of the probe tip onto the centre of the visible surface of the calculus. As a result, however, a variation of the direction of sight against the uretral wall is brought about. This effect is intensified by an inside bulging of the uretral wall which is not expanded between the urethrolith and the distal end of the ureteroscope, which bulging is always present, so that the tip of the probe and the calculus often disappear completely from the visual field and therefore a crushing of the calculus under sufficient visual control is often impossible.

The present invention is based on the problem of providing a metal probe of the type mentioned by way of introduction, which is suitable for intracorporeal lithotripsy and which allows for avoidance of a propulsion of the calculi relative to the joining ureter when calculi, specifically urethroliths, are crushed, and which should also allow, at the same time, for achievement of sight onto the calculus when a lithotripsy operation is performed by means of a conventional ureteroscope.

In accordance with the present invention this problem is solved in a metal probe of the general type defined by the introductory clause of Patent claim 1, by the provision that the tip of the probe is provided with at least one lateral notch near the probe end, which notch is configured for a laterally oriented fixation of a calculus to be crushed against a joining duct wall.

On account of the notch formed on the tip of the probe or expediently of a plurality of such notches along the tip of the probe, hence the possibility is achieved in the inventive metal probe to maintain a urethrolith, which is initially fixed against the uretral wall, in a continuously fixed position throughout the calculus crushing operation by the application of a slight lateral pressure via the probe onto the calculus so that, as a result, a propulsion of the calculus will be avoided during the calculus crushing operation. Due to the lateral arrangement of said one notch or several notches the advancing movement of the probe through the lumen of the ureteroscope remains, at the same time, unhindered and moreover the possibility is retained to perform an operation of calculus crushing in a manner so far common, using a probe end having a substantially blunt probe tip, wherein the tip of the probe is guided in a direction substantially orthogonal on the calculus rather than laterally against the calculus.

Further advantageous and expedient configurations of the inventive metal probe become apparent from the dependent claims.

One embodiment of the invention is illustrated in a schematic view in the drawing and will be explained in more details in the following. In the drawing:

FIG. 1 is a schematic illustration of the tip of the probe,

FIG. 2 shows a sectional view of the probe tip along the line II—II in FIG. 1,

Figure 4:
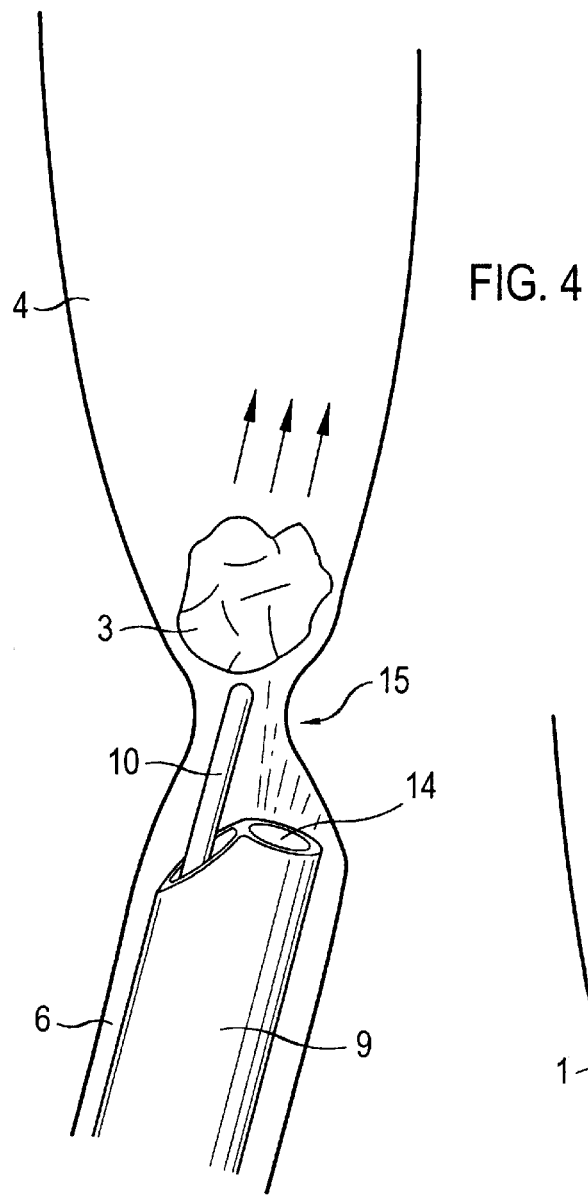
Figure 5:
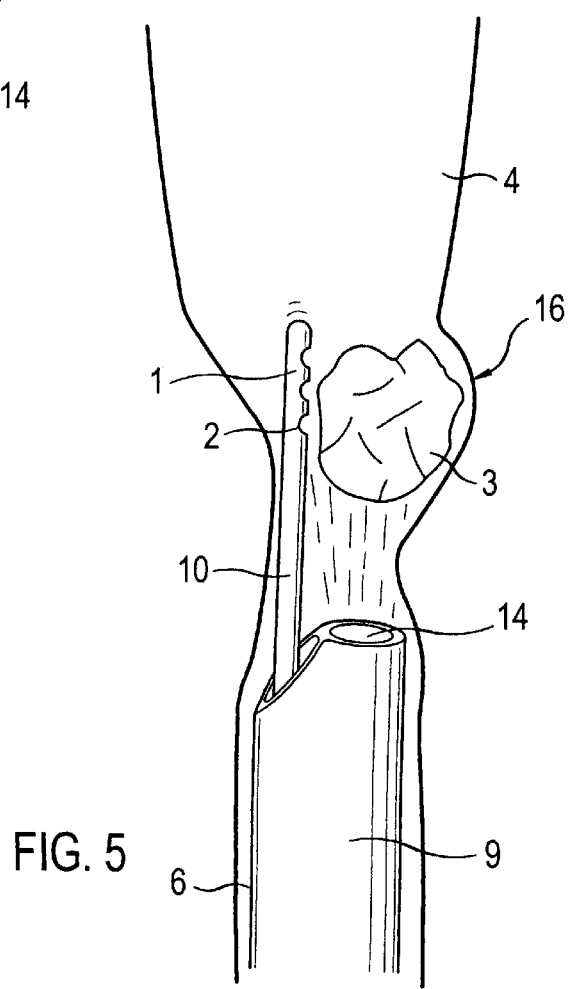

FIG. 3 is a schematic view for explanation of the operation of crushing a urethrolith, using an inventive probe which is inserted into the lumen of an ureteroscope, FIG. 4 shows a schematic view for explanation of the operation of crushing a urethrolith, using a probe according to prior art, and FIG. 5 is a schematic illustration for explanation of the operation of crushing a urethrolith, using an inventive probe.

According to the illustration in FIG. 1 a metal probe 10 having a circular cross-section and suitable for use in intracorporeal shock wave lithotripsy is configured to have a probe tip 1 on its distal end, which presents lateral notches 2. The notches 2 are formed as cylinder segments so that a cross-section of the probe is achieved which has the shape of a segment of a circle, as is illustrated in FIG. 2. The depth of each notch is so dimensioned that the tip of the probe cannot break at this location. Each notch may also be configured as a segment of a right parallelepiped or as a polygon or even with a saw-tooth shape, rather than being configured as cylinder segment. A combination among these different configuration is conceivable, too, on the condition that not only at least one notch but several notches are provided which present the same orientation and are aligned along a common surface line of the probe in parallel with the latter's longitudinal axis.

For crushing a urethrolith 3, for instance, which is caught in a ureter according to the illustration in FIG. 3, the probe 10 is inserted into the lumen of a ureteroscope 9 used in this operation. The probe 10 is held by means of the handpiece 11 of a lithotripter which may have a configuration in accordance with the European Patent EP 0 317 507, for example. In these lithotripters a pneumatically driven impact element produces an impact energy which is transferred to the probe by the latter's proximal end for transmission, which results from the generation of a shock wave passing through the probe. Apart therefrom, the probe may also be used in lithotripters in which a comparable impact element is driven hydraulically or even by electromagnetic means.

The urethrolith 3 is fixed in its position in which an upper section of the ureter is distinctly expanded as a consequence of the banking effect produced by the urine flowing in from the kidney 5. A lower section 6 of the ureter is connected to the urinary bladder 7, with the distal end of the ureteroscope being introduced into the respective opening 8 of the ureter so far that the tip of the probe 10, which projects beyond this distal end, is positioned in the vicinity of the urethrolith 3 to be crushed. This positioning of the tip of the probe may be viewed via an eyepiece 12 of the ureteroscope 9.

The schematic illustration in FIG. 4 shows the conditions which may be present when the urethrolith 3 is crushed, if a probe of a conventional design is used which has a comparatively blunt tip. When the distal end of the ureteroscope 9 is advanced the lower section of the ureter 6 undergoes an expansion(bouginage) so that a circular inside bulging 15 occurs as a consequence in the vicinity of the urethrolith 3. As a result of this inside bulging an impairment of the visual field of the optical system 14 of the ureteroscope 9 occurs, which may be even intensified additionally when an attempt is made to orient the tip of the probe towards the centre of the calculus 3, for an optimum crushing of the calculus, and to this end the distal end of the ureteroscope 9 is then tilted out of the longitudinal axis of the section of the ureter 6. On account of this tilting motion the fixing of the calculus may become loose at the same time so that the calculus undergoes a displacement into the expanded section 4 of the ureter, with simultaneous occurrence of calculus propulsion into this upper ureter section as soon as the operation of calculus crushing proper commences and a uniform straight movement of the tip of the probe occurs as a consequence of the shock waves passing through the probe.

The schematic illustration in FIG. 5 shows the comparable conditions which occur when the urethrolith 3 is crushed by the application of a probe in which the tip of the probe 1 is provided with the inventive notches 2. Due to the lateral arrangement of these notches 2 now a laterally oriented fixation of the calculus 3 against the joining uretral wall can be achieved with an appropriate guidance of the distal end of the ureteroscope 9 through the lower section 6 of the ureter, which fixation is maintained also for the operation of calculus crushing which is now initiated via these notches. With a slight pressure being simultaneously exerted by means of the probe tip against the calculus, and with an outside bulging 16 of the uretral wall being achieved due to this pressure, the visual field of the optical system 14 of the ureteroscope 9 is extended, too, on the other hand, so that also the operation of calculus crushing proper can be performed under correspondingly improved viewing conditions, apart from the prevention of calculus propulsion during the operation with the inventive probe. These viewing conditions may, by the way, be additionally optimised by the provision that the probe tip is made dark or light-absorbing, with the exception of the notches, and that the notches are made light or light-reflective so that the best light conditions will be present directly on the location where the operation of calculus crushing starts. Due to the lateral arrangement of the notches it is ensured, by the way, that the tip of the probe still presents a continuous generated surface which is large enough to prevent any lesion in the region of the uretral wall where the calculus remains unfixed.

What is claimed is:

1. A metal probe adapted to be introduced into the lumen of an endoscope, a tip of the probe comprising at least one notch, wherein the probe has an elongated shape comprising a lateral outer circumferential surface, and wherein the notch is positioned on the lateral circumferential outer surface wherein the at least one notch of the probe is used for crushing calculi by longitudinal oscillation of the probe tip and fixating calculi against a joining duct wall, and wherein the notch presents a saw-tooth configuration.

2. The probe of claim 1 wherein the probe tip comprises more than one notch and all of the notches are oriented in the same direction relative to the longitudinal axis of the probe and wherein said notches are configured to be aligned along a surface line parallel with the longitudinal axis of the probe.

3. The probe of claim 2 wherein said notches are arranged at mutual spacings and that the nominal diameter of the probe tip is retained for gaps between said notches.

4. The probe of claim 2 wherein the tip of the probe, with the exception of said notch or notches, is made dark or light-absorbing, respectively, and that said notches are made light or light-reflecting, respectively.

5. The probe of claim 1 wherein the probe has a cylindrical shape.

6. The probe of claim 1 wherein the probe comprises a rounded end.

7. A method for crushing a calculus in a lumen of a human body comprising:

introducing a metal probe into an endoscope, wherein the metal probe has an elongated shape comprising a central axis parallel to a lateral outer circumferential surface, a tip of the probe comprising at least one notch positioned in the lateral circumferential surface;

advancing the tip of the probe through the endoscope;

positioning the tip of the probe adjacent the calculus, wherein the at least one notch is directed against the calculus and the calculus is positioned between a lumen wall and the at least one notch; and applying pressure to the tip of the probe to fix the position of the calculus against the lumen wall.

8. The method of claim 7 further comprising oscillating the probe longitudinally along the central axis of the probe.

9. The method of claim 7 further comprising oscillating the probe using an impact energy device.

* * * * *